United States Patent
Insall et al.

[11] Patent Number: 6,068,658
[45] Date of Patent: May 30, 2000

[54] PROSTHESIS FOR KNEE REPLACEMENT

[75] Inventors: John Nevil Insall, New York, N.Y.; Peter Stanley Walker, Middlesex, United Kingdom; Jonathan Blamey; Michael Wadcock, both of Wiltshire, United Kingdom

[73] Assignee: Zimmer Ltd., Wilts, United Kingdom

[21] Appl. No.: 09/037,051

[22] Filed: Mar. 9, 1998

[30] Foreign Application Priority Data

Mar. 13, 1997 [GB] United Kingdom .................. 9705161

[51] Int. Cl.[7] ...................................................... A61K 2/33
[52] U.S. Cl. .............................................................. 623/20
[58] Field of Search ................................................. 623/20

[56] References Cited

U.S. PATENT DOCUMENTS

| | | | |
|---|---|---|---|
| 4,209,861 | 7/1980 | Walker et al. | 623/20 |
| 5,147,405 | 9/1992 | Vanzile | 623/20 |
| 5,344,423 | 9/1994 | Dietz et al. . | |
| 5,344,461 | 9/1994 | Phlipot . | |
| 5,395,377 | 3/1995 | Petersen et al. . | |
| 5,472,415 | 12/1995 | King et al. . | |
| 5,683,468 | 11/1997 | Pappas | 623/20 |
| 5,702,466 | 12/1997 | Pappas et al. | 623/20 |
| 5,782,925 | 7/1998 | Collazo et al. | 623/20 |
| 5,871,545 | 2/1999 | Goodfellow et al. | 623/20 |
| 5,879,392 | 3/1999 | McMinn | 623/20 |
| 5,879,394 | 3/1999 | Ashby et al. | 623/20 |
| 5,906,643 | 5/1999 | Walker | 623/20 |
| 5,928,286 | 7/1999 | Ashby et al. | 623/20 |
| 5,935,173 | 8/1999 | Roger et al. | 623/20 |

FOREIGN PATENT DOCUMENTS

| | | |
|---|---|---|
| 689 796A1 | 1/1996 | European Pat. Off. . |
| 2 280 375A | 2/1995 | United Kingdom . |
| WO 96/25123 | 8/1996 | WIPO . |

*Primary Examiner*—Paul J. Hirsch
*Attorney, Agent, or Firm*—Burns, Doane, Swecker & Mathis LLP

[57] ABSTRACT

The prosthesis comprises a femoral component (2) having at least one substantially spheroidal condylar bearing surface (10,11), a tibial component (6) including a tibial platform (20), and a plastics meniscal component (7) located between the condylar bearing surface (10,11) an the tibial component (6) and being slidable on the platform (20). The meniscal component (7) is retained on a guide (23) upstanding from the platform (20). The guide (23) includes a post (24) and a cap (25) which is a snap-fit in a recess (30) in the meniscal component (7). The guide (23) is slidable in a track (32) within the meniscal component (7) so that movement of the meniscal component (7) in the anterior/posterior direction (A–P) is limited by impingement of the meniscal component (7) on the post (24) and/or on a rail member (21) projecting from the surface of the tibial platform (20). To install the prosthesis, a femur (1) is resected to provide a base for receiving the femoral component (2), which is retained in the resected femur by pins (3). The tibia (4) is resected to provide a flat base into which the tibial component (6) is fixed by a stem (5).

9 Claims, 5 Drawing Sheets

PROSTHESIS FOR KNEE REPLACEMENT

Reference is made to our U.S. patent application No 08/898,360 now U.S. Pat.No. 5,989,261, filed Jul. 29, 1997, which describes a method of evaluating the fit of a knee prosthesis. The disclosure of this application is incorporated herein by reference.

This invention relates to prostheses for knee replacement, particularly those intended for total knee replacement.

UK Patent Application No. 9414247.8 (Publication No. 2280375) describes a prosthesis of the condylar replacement type, comprising a femoral component, a tibial base plate and a plastic meniscal component arranged to support the femoral component and to slide on the base plate. In the above UK application, the meniscal component is guided on a rail or stud upstanding form the base plate, so as to constrain movement of the meniscal component substantially in an anterior/posterior direction, while allowing rotational freedom of at least about ±15°. The guide member is received in a slot in the meniscal component and limits on the displacement of the meniscal component in the anterior/posterior side of the base plate and abutment of the upstanding metal stops on the posterior side of the base plate and abutment of the guide on the end of the slot in the plastics component in the anterior direction.

In one embodiment described in the above application, the stud takes the form of a post having a circular metal cap.

The present invention provides further improvements in the design described in the above application.

There are several considerations in the design of prostheses of this kind. One of these is to provide a system where dislocation of the plastics component is avoided at all times. Another requirement is that the plastics component should not jam on the guide in its movements in the anterior/posterior direction and, thirdly that the plastics component should not be capable of being assembled incorrectly when installing the prosthesis in the patient.

It is towards the solution of the above problems that the present invention is primarily directed.

According to one aspect of the present invention there is provided a prosthesis for knee replacement which comprises:

(a) the femoral component having at least one condylar bearing surface (preferably spheroidal), (b) a tibial component including a tibial platform, (c) a plastics meniscal component located between the condylar bearing surface and the tibial component, and being mobile on the platform, said meniscal component being retained on a guide upstanding from the platform, said guide including a post and a cap, which cap is a snap-fit in a recess in the meniscal component and is mobile in a track within the meniscal component, wherein sliding movement of said meniscal component in the anterior/posterior direction (A–P) is limited by impingement of the meniscal component on said post and/or on a rail member projecting from the surface of the tibial platform.

Preferably, the displacement of the meniscal component in the anterior direction is limited by a rail forming an abutment at or close to the anterior edge of the tibial platform. The rail generally should provide an upstanding vertical surface, substantially at right-angles to the A–P sliding direction of the meniscal component.

Posterior displacement of the meniscal component is controlled by the guide sliding within the track in the meniscal component. In order to prevent jamming occurring at any time during relative sliding movement or rotational movement of the meniscal component on the tibial platform, the dimensions of the cap are selected so that there is a clearance between the periphery of the cap and the corresponding size of the opening in the meniscal track. The length of the track is also preferably selected so that the periphery of the cap does not impinge on the inner wall of the cavity within the meniscal component at any point in its movement.

Thus, for example, anterior movement of the meniscal component is limited by abutment of the anterior face of the meniscal component on the anterior rail, forming a limit stop in the anterior direction. In the posterior direction, movement is arrested by abutment of the meniscal component on the post supporting the cap. Thus, at the limits of movement in the A–P direction, the periphery of the cap come into contact with the end wall of the track within the meniscal component. It will be appreciated that because the diameter of the post will be smaller than the hole (at least at some points), in the meniscal component which gives access to the recess, the cap can limit medial/lateral movement of the meniscal component in some positions, by contacting the side walls of the recess.

The dimensions of the cap and of the recess in the underside of the meniscal component comprising the track are selected so that the plastics component can be snapped over the stud. This is generally assured by manufacturing the recess so as to be of the same planar maximum dimension as the cap, or up to 0.5 mm smaller. Preferably, the recess is manufactured to be between about 0.2 and 0.3 mm smaller than the cap.

The cap is preferably manufactured to be asymmetrical about at least one plane passing axially through the post, and to provide a generally corresponding shaped opening in the plane of the underside of the meniscal component. In this way, the meniscal component is capable of assembly in the tibial platform in only one orientation. This avoids the danger that the meniscal component may be accidentally assembled the wrong way round on the tibial guide stud.

In a preferred construction, the cap on the tibial stud has a flat face which is parallel with the rail on the tibial platform and the rail is positioned as an anterior stop.

Rotation of the meniscal component on the tibial base plate is permitted within limits determined by the abutment of the anterior face of the meniscal component with the anterior rail on the tibial platform. In order to reduce the chance of accidental dislocation of the plastics component from the tibial platform, the recess and the tibial guide stud are orientated so that the snap-fit occurs at a point in the orientation of the plastics component on the base plate, which is the least likely point at which dislocation of the meniscal component from the tibial tray may occur.

Dislocation of the femoral component from the meniscal component is most likely where the meniscal component is at or near the posterior limit, and the femoral component is hyper-extended. At this point, there is a maximum moment tending to lift the meniscal component off the base plate. As a protection against hyper-extension of the prosthesis, the meniscal component is formed with a saddle positioned generally posteriorly of the centre point. This saddle has a substantially vertical face on the anterior side, which is engaged with an intercondylar bridge portion between the two condylar spheroidal surfaces. This contact between the bridge portion of the femoral component and the saddle provides a positive stop after the femoral component passes through the zero degree position.

On one side at least of the saddle projection, a vertical face is provided in order to provide medial/lateral stability to the femoral component. However, it is preferred that at the medial side of the prosthesis, the lateral face of the saddle projection slopes into the spheroidal cavity in order to avoid point loading of the plastics member should the femoral component be tilted internally.

Further features and advantages of the present invention will become apparent from the following description in connection with the accompanying drawings, in which.

Figure 1A:
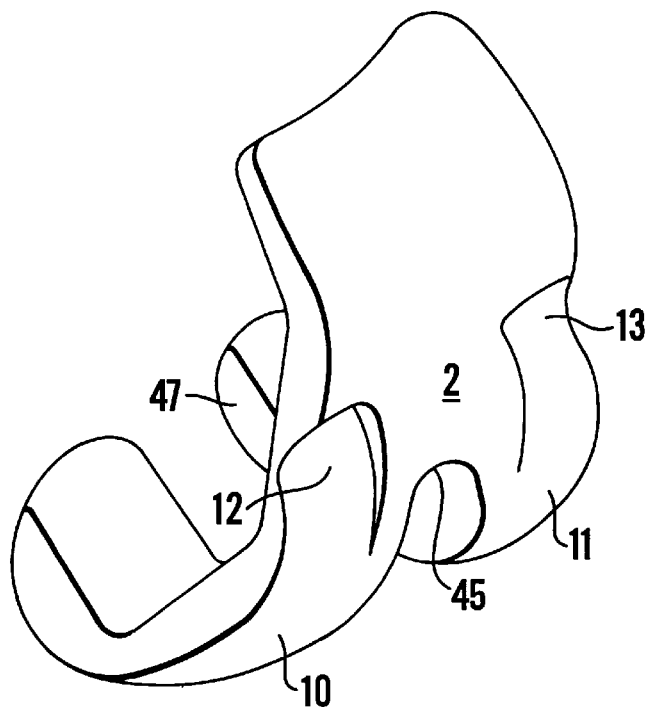
FIG. 1A is a perspective view of the femoral component.
Figure 1B:
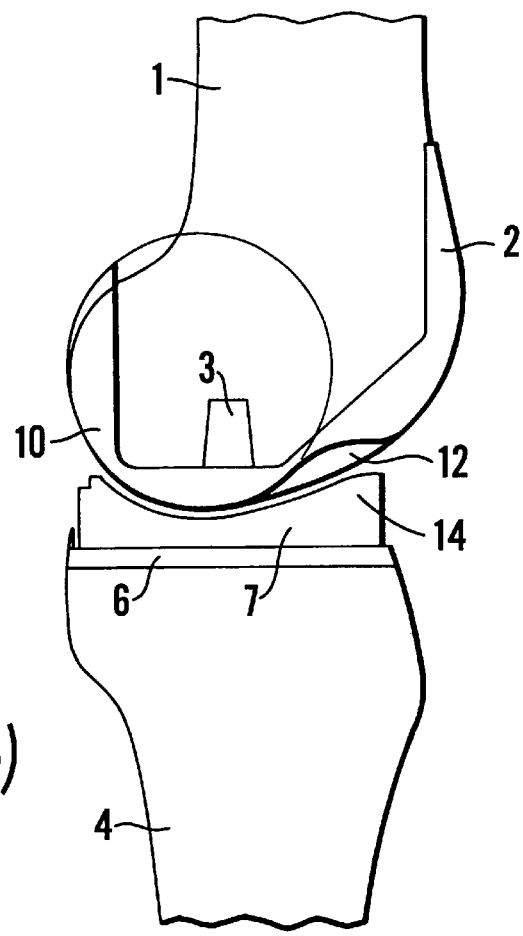
FIG. 1B is a schematic sagittal view of the prosthesis in place.

Referring to FIG. 1B of the drawings, a femur 1 is resected to provide a base for receiving the femoral component 2, which is retained in the resected femur by pins 3. The tibial 4 is resected to provide a flat base into which the tibial component is fixed by a stem 5, to provide a generally flat tibial base plate 6 with a 5–7° posterior slope. A meniscal plastics component 7 is interposed between the tibial base plate 6 and the femoral component 2, and the condylar articulating surfaces 10 and 11 of the femoral component 2 are preferably spheroidally shaped and preferably are closing conforming. The femoral component 2 is shaped with notches 12 and 13, designed to be engaged by meniscal anterior upsweep portions 14 to provide a whole or partial hyper-extensive stop.

Figure 6:
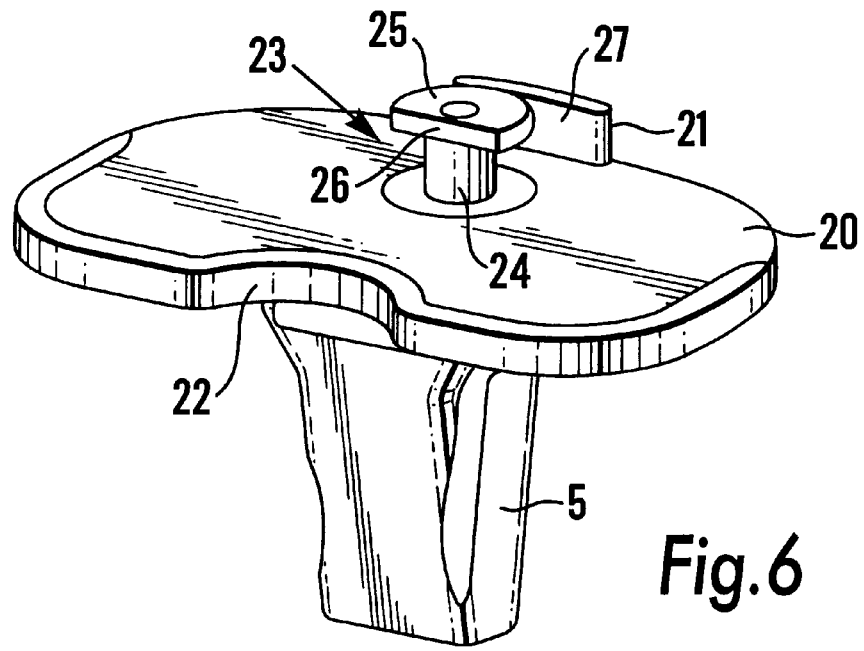
FIG. 6 is a perspective view showing the tibial component and the guide stud.

The tibial component is shown in perspective view in FIG. 6, from which it can be seen that it comprises a generally flat platform 20 supported on the stem 5. Upstanding from the anterior face of the tibial platform is a rail 21 which, as will be explained later, provides an anterior positive stop for the anterior displacement of the meniscal component.

The posterior side of the tibial platform is cut away at 22 to allow for retention of the posterior cruciate ligament, and an upstanding guide 23 is provided for retaining the meniscal component of the tibial platform and for guiding the plastics component for limited sliding movement on the platform. The guide 23 comprises a post 24 and a cap 25. The cap 25 is fixed to the top of the post and has a flat face 26 in the posterior direction, which is substantially parallel to the face 27 of the anterior stop.

Although the cap is shown to be D-shaped, other designs are possible. The cap should preferably be asymmetrical about at least one plane passing axially through the guide post, but preferably extends in at least two directions in the plane parallel to the tibial platform, so that it will provide resistance to the meniscal component lifting up, when the meniscal component is in or close to its maximum posterior position and is, therefore, subjected to the greatest tipping movement.

Various shapes such as triangular, quadrilateral or polygonal may be employed, although we currently prefer to employ one flat side while the remainder of the cap has a curved perimeter.

Figure 5:
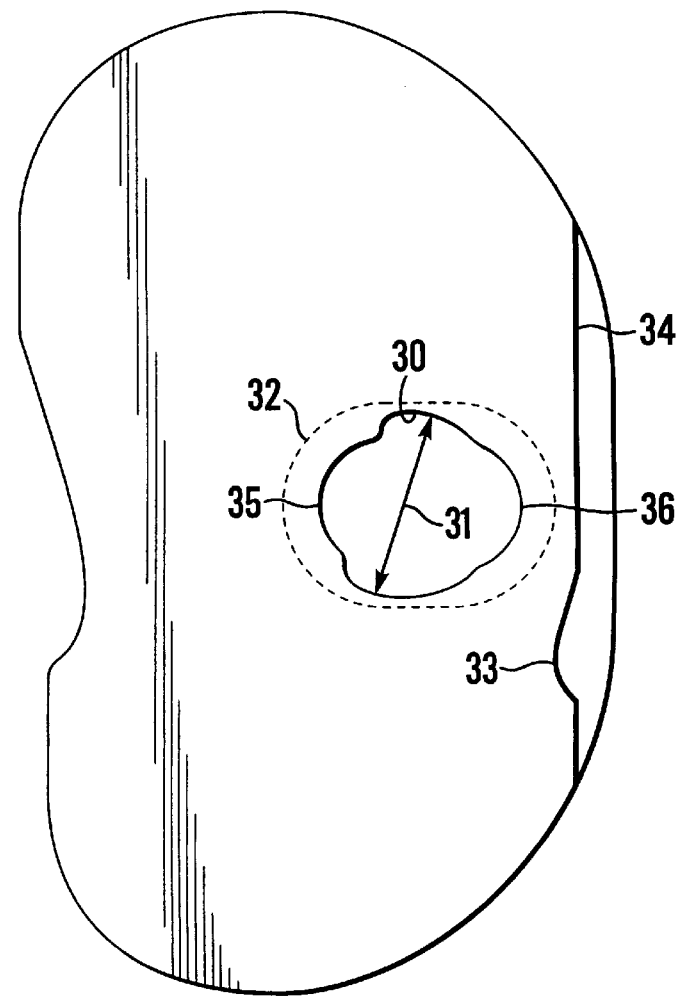
FIG. 5 is an underside view of the meniscal component showing the recess for receiving the guide stud.

The recess within the meniscal component is shown in FIG. 5, and it will be seen that the recess 30 is of a regular form and is designed so that the cap can be snapped into place at only one relative orientation between the meniscal component and the tibial base plate. This is achieved by selecting a maximum dimension 31 across the recess which corresponds precisely with or is within 0.5 mm of the corresponding maximum dimension across the cap of the guide cap. This ensures that it is not possible to assemble the meniscal component the wrong way round.

As clearly seen in FIG. 5, the recess 30 gives access to a slot 32 which is closed at both ends but when the cap 25 is received within the slot, the cap extends therein and prevents the cap being lifted off. In order to facilitate assembly, a guide notch 33 may be formed in the anterior face of the plastics component. When this notch is orientated so that it is pressed hard against one edge of the rail member 21, the surgeon knows that the cap is aligned for entry into the recess.

Movement of the plastics component on the tibial base plate is illustrated in FIGS. 8A to 8D. As can be seen, this permits internal rotation up to about 17° and external rotation up to about 10°. Rotation is limited by impingement of the cut-away portion 34 of the anterior face of the plastic component, with the anterior rail 21 and by the abutment of the post 24 against the forward or rearward end of the recess 35 or 36. The notch 33 allows further rotation in the internal direction. It is to be noted that the overall dimension of the cap and the internal dimension of the slot 32 is selected so that there is some freedom of movement of the cap within the slot 32. In general, there is always a gap of at least about 0.2 mm. This reduces the chances of jamming of the meniscal component on the guide.

Figure 8A:
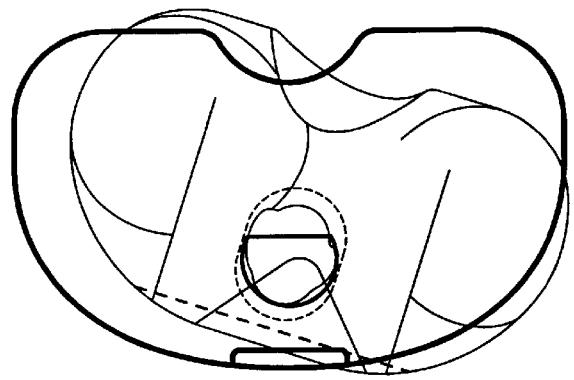
FIGS. 8A to 8D show various relative positions of the meniscal component on the tibial base plate.
Figure 8B:
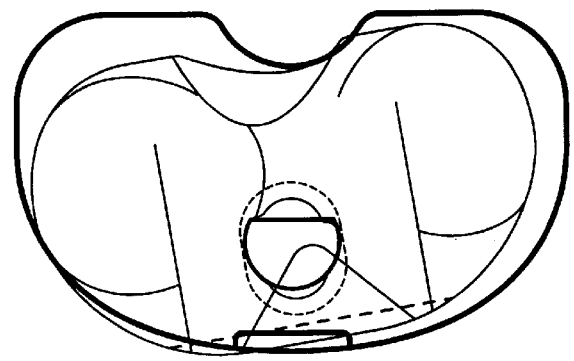
Figure 8C:
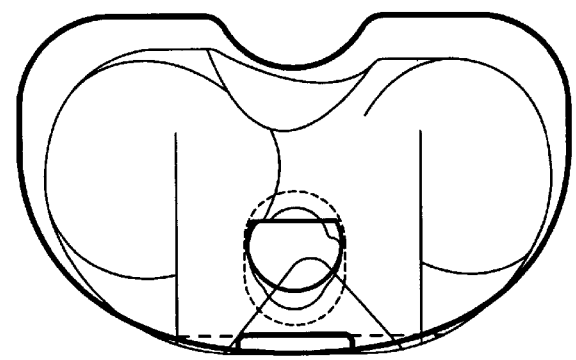
Figure 8D:
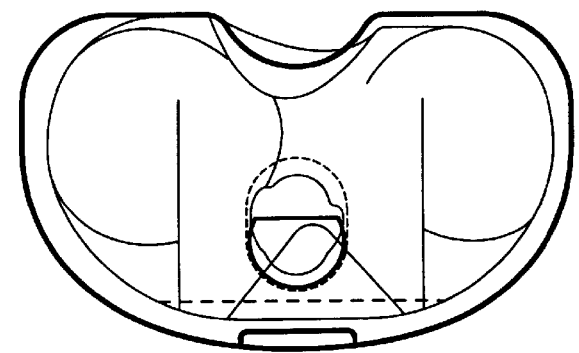

The laxity in this respect in various positions of the meniscal component on the tibial base plate is illustrated in FIGS. 8A to 8B.

Figure 7:
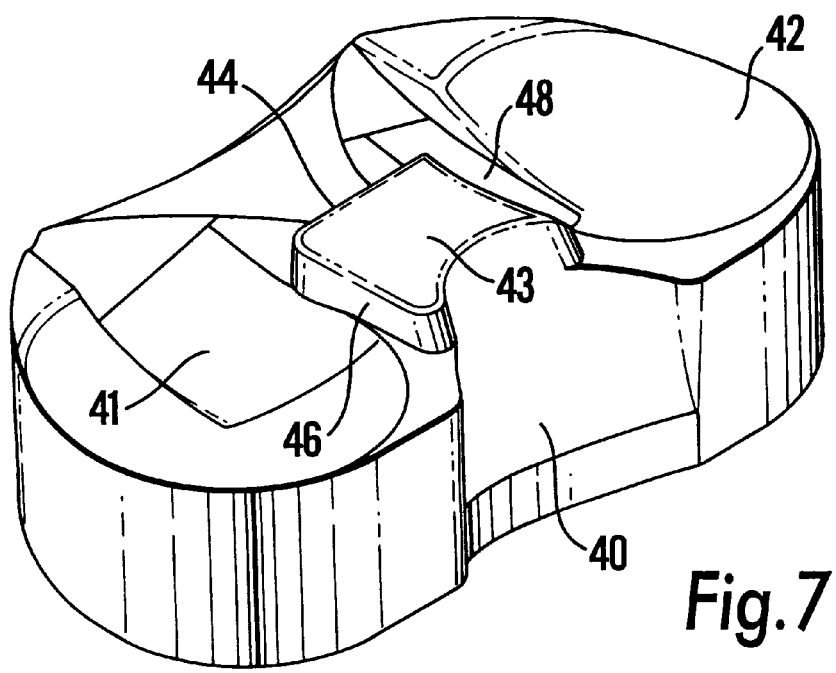
FIG. 7 is a perspective view of the meniscal component.

The meniscal component itself is shown in perspective view in FIG. 7. It will be noted that the posterior surface has a sloping face 40 which permits the posterior cruciate ligament to pass alongside the posterior of the prosthesis without abrasion. Moulded generally posteriorly between the dished bearing surfaces 41 and 42 is a saddle 43. The saddle has an anteriorly facing generally vertical wall 44, which is intended to engage in the fork 45 (see FIG. 1A) of the femoral component, and to limit the rotation and translation of the femoral component on the meniscal component in hyper-extension.

At the same time, the saddle 44 incorporates a lateral, substantially vertical wall 46 alongside the inner face 47 of the corresponding side of the femoral component during flexion. This provides for enhanced stability of the femoral component on the meniscal component in a medial/lateral direction. On the medial side, the saddle has a sloped face 48 which merges into the spheroidal-shaped depression 42. This ensures that should the femoral component tilt and pivot inwardly on the meniscal component, the articulating surfaces 42, 10 and 11 would not be subjected to point loading. This kind of movement occasionally occurs if the collateral ligaments are not balanced and, in such cases, there is a tendency for the femur to be tipped inwardly.

Figure 2:
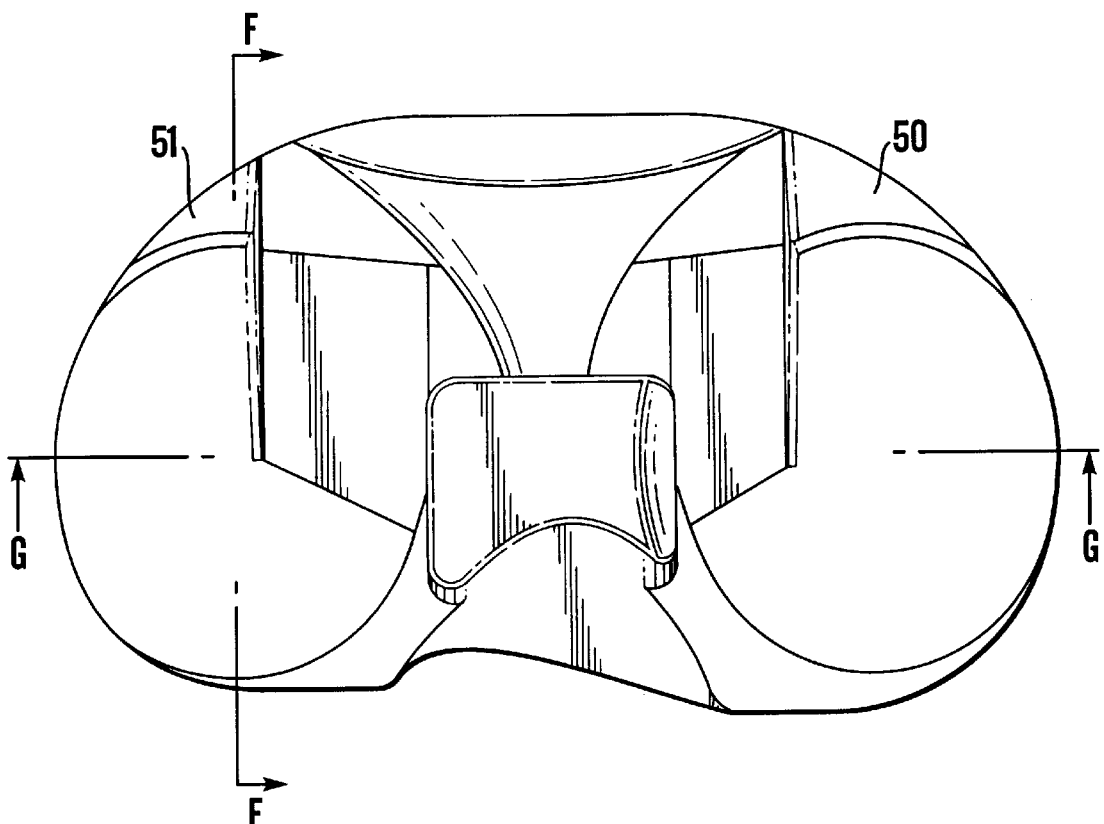
FIG. 2 is a plan view of the meniscal component.
Figure 3:
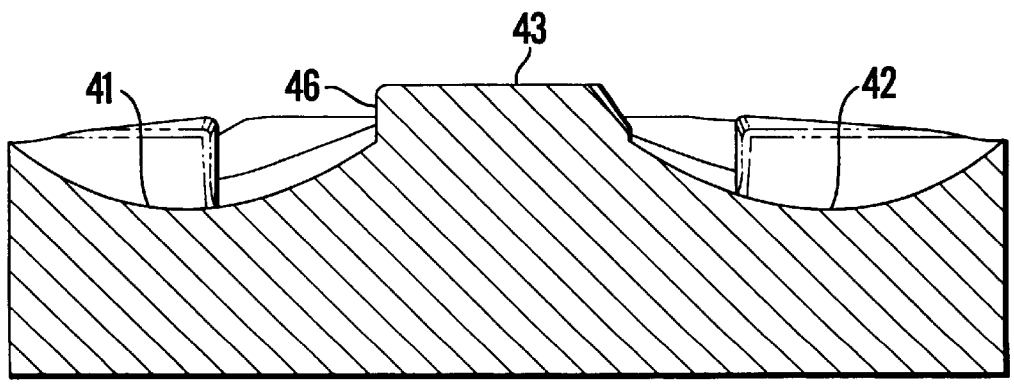
FIG. 3 is a section along the line G—G in FIG. 2.
Figure 4:
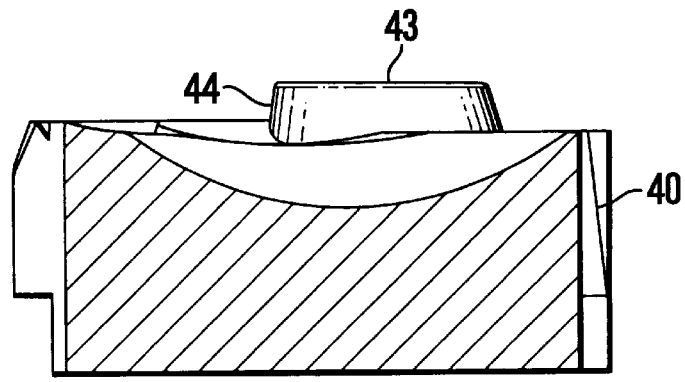
FIG. 4 is a section along the line F—F in FIG. 2.

In order to render the meniscal component radiopaque, the meniscal component can be provided with sealed holes containing a heavy metal such as tantalum in a part of the plastic which will not contact the metal femur. This may, for example, be points 50 and 51 as shown in FIG. 2, and this will enable the surgeon to determine correct location and movement of the component after installation of the prosthesis.

What is claimed is:

1. A prosthesis for knee replacement which comprises:
   (a) a femoral component having at least one substantially spheroidal condylar bearing surface,
   (b) a tibial component including a tibial platform,
   (c) a plastics meniscal component located between the condylar bearing surface and the tibial component and being slidable on the platform, said meniscal component being retained on a guide upstanding from the platform, said guide including a post and a cap said cap is a snap-fit in a recess in the meniscal component and is slidable in a track within the meniscal component, wherein sliding movement of said meniscal component in the anterior/posterior direction is limited by impingement of the meniscal component on said post or on a rail member projecting from the surface of the tibial platform.

2. A prosthesis according to claim 1 wherein the cap is asymmetrical about at least one plane passing axially through the post and said recess has a correspondingly shaped opening in the plane of the underside of the meniscal component, whereby the meniscal component is capable of assembly on the tibial platform in only one orientation.

3. A prosthesis according to claim 1 wherein the cap when viewed in plan view, has a flat side on one face which is parallel with said rail projecting from the tibial platform and positioned as an anterior stop.

4. A prosthesis according to claim 3 wherein the cap is substantially 'D'- shaped in plan, the flat side being substantially parallel with said rail.

5. A prosthesis as claimed in claim 1 wherein the meniscal component includes a saddle, one lateral face of which is substantially upright, said lateral face being positioned to interact with a surface on the femoral component to enhance medial/lateral stability of the prosthesis.

6. A prosthesis for knee replacement which comprises:
   (a) a femoral component having at least one substantially spheroidal condylar surface,
   (b) a tibial component including a tibial platform,
   (c) a plastic meniscal component located between the condylar bearing surface and the tibial component and being moveable on the platform said meniscal component being retained on a guide upstanding from the platform, said guide including a post and a cap which are fixed relative to the platform, the cap being received in a recess in the meniscal component and slidable in a track therein in the anterior-posterior direction, the cap being asymmetrical about at least one plane passing axially through the post and the recess having an opening which is so shaped that the meniscal component can be assembled onto the guide in a limited number of relative orientations of the meniscal component and the platform when the track does not lie in the anterior-posterior direction.

7. A prosthesis as claimed in claim 6 wherein the meniscal component can be assembled onto the guide in only one relative orientation of the meniscal component and the platform.

8. A prosthesis as claimed in claim 6, wherein the meniscal component can be assembled onto the guide in a limited number of relative orientations of the meniscal component and the platform only when the track does not lie in the anterior/posterior direction.

9. A prosthesis for knee replacement which comprises:
   (a) a femoral component having at least one substantially spheroidal condylar surface,
   (b) a tibial component including a tibial platform,
   (c) a plastic meniscal component located between the condylar bearing surface and the tibial component and being movable onto the platform, said meniscal component being retained on a guide upstanding from the platform, said guide including a post and a cap, the cap being received in a recess in the meniscal component and slidable in a track therein, the cap being asymmetrical about at least one plane passing axially through the post and the recess having an opening which is so shaped that the meniscal component can be assembled onto the guide in a limited number of relative orientations of the meniscal component and the platform, and the cap, when viewed in plan view, having one flat side which is parallel with an abutment projecting from the platform and positioned as an anterior stop for the meniscal component.

* * * * *